United States Patent [19]

Klein et al.

[11] 4,397,702
[45] Aug. 9, 1983

[54] FABRICATION OF NON-CONDUCTIVE CHARGED SENSING PROBE UNIT

[75] Inventors: Carl F. Klein, New Berlin; Stuart R. Buchanan, Mequon; Paul E. Thoma, Burlington; David L. Klimek, Milwaukee, all of Wis.

[73] Assignee: Johnson Controls, Inc., Milwaukee, Wis.

[21] Appl. No.: 341,320

[22] Filed: Jan. 21, 1982

Related U.S. Application Data

[63] Continuation-in-part of Ser. No. 110,635, Jan. 9, 1980, abandoned.

[51] Int. Cl.³ .............................................. B05D 5/12
[52] U.S. Cl. .................................... 156/153; 156/60; 156/273.1; 156/281; 156/308.2; 427/35; 427/58; 427/185; 427/195; 427/250; 427/374.2; 427/374.3; 427/374.4; 427/375; 427/379; 427/388.1; 307/400; 29/592 E; 29/399
[58] Field of Search .................... 307/400; 179/111 E; 427/35, 58, 10, 185, 195, 374.2, 374.3, 374.4, 375, 379, 388.1, 250, 322, 327; 156/60, 153, 273, 281, 308.2

[56] References Cited

U.S. PATENT DOCUMENTS

| | | |
|---|---|---|
| 2,844,489 | 7/1958 | Gemmer ............................ 427/185 |
| 3,189,802 | 6/1965 | Zisman ............................. 361/289 |
| 3,208,868 | 9/1965 | Strobel et al. ..................... 427/10 |
| 3,851,183 | 11/1974 | Lewiner et al. .................. 307/400 |
| 3,924,324 | 12/1975 | Kodera ............................. 307/400 |
| 4,037,310 | 7/1977 | van Turnhout ................... 307/400 |
| 4,127,681 | 11/1978 | Ferren et al. ..................... 307/400 |

Primary Examiner—Michael R. Lusignan
Assistant Examiner—Richard Bueker
Attorney, Agent, or Firm—Andrus, Sceales, Starke & Sawall

[57] ABSTRACT

A sensing probe unit includes an electrically nonconductive polymeric layer charged with a permanent electric charge to form an electret and intimately bonded to a compensating metal electrode. In the fabrication, the polymeric layer is cleaned and the metal electrode affixed to one surface by vapor deposition, lamination or baking. The polymeric layer may also be applied by coating the electrode with dielectric particles and then heating the subassembly to fuse the particles into an integral layer and to bond the fused layer to the electrode. The subassembly is thermally destressed and the polymeric layer is thereafter charged by triboelectric charging, corona discharge or electron beam charging, or by liquid contact charging processes. In the latter, a Freon-type or other similar liquid having good wetting properties and high evaporation rate is used as a contact charging liquid which creates a particularly stable electret. The sensing probe is stored to prevent loss of charge and sensitivity. The sensing probe unit in a pollutant and combustion detection apparatus is mounted within a suitable apertured ground shield unit with an exposed dielectric sensing surface to form an electrostatic sensor or a capacitor sensor. The compensating electrode is connected to a high impedance detection amplifier.

41 Claims, 9 Drawing Figures fig. 1 fig. 3 fig. 2a fig. 2 fig. 4 fig. 5 fig. 6 fig. 7 fig. 8

FABRICATION OF NON-CONDUCTIVE CHARGED SENSING PROBE UNIT

This application is a continuation-in-part of application Ser. No. 06/110,635, filed Jan. 9, 1980 now abandoned.

BACKGROUND OF THE INVENTION

This invention is related to fabrication of a detection or sensing probe unit and particularly to such a sensing probe unit which is particularly useful for detecting environmental borne constituents generated as a result of combustion, pollution or the like.

Combustion detection and alarm systems employing various sensing and detecting means have been suggested, such as thermal, flame, photo-electric, ionization chamber, semiconductors of a metal oxide or polymeric organic material, and electrolyte cell sensors. A particularly satisfactory apparatus is disclosed in the copending application of the present inventors entitled Charged Non-Conductive Polar Sensing Element and Detection System filed on Oct. 11, 1978 with Ser. No. 950,413. The system disclosed therein includes an improved sensing element which includes a sensitive charged non-conductive sensing layer affixed to a metal plate which also serves as the terminal means for connection with a detection circuit. The sensing layer is preferably a polymeric material which has a surface resistivity in excess of $1 \times 10^{10}$ ohms/square at 50% RH (relative humidity) and a bulk resistivity in excess of $1 \times 10^{12}$ ohm cm at 50% RH and which is essentially free of polar substances. The layer includes either an internal and/or surface charge to establish a high intensity electric field. The electret sensing element, either connected as an electrostatic probe or as one plate of a capacitor sensing unit, provides practically instantaneous response to the presence of products of combustion. The electret sensing element will sense early generated aerosol components such as toxic polar gases as well as the particulate and charged particles, all of which may occur in different degrees at the incipient stage of combustion depending upon the particular combustion materials. Electrets are known elements and have been formed in various procedures.

As disclosed in the above application, the preferred polymeric electret materials generally include polytetrafluoroethylene (Teflon TFE), polystyrene, and polyethylene, all of which have a dipole-hydrogen bonding force value of surface energy of less than 1 ergs/cm$^2$. The electret includes a detection surface which forms part of a free space exposed to the products of combustion at the incipient stage of combustion and in particular, including the toxic and noxious gases produced by the process of combustion. The detection appears dependent upon the ability of the electret surface to adsorb polar gas molecules generated by combustion, with the charged probe producing significant amplification in response to the resulting induced charge which can be detected. The charged probe or electrode also has the ability to attract charged ion radicals, aerosols, polar gas molecules and the like associated with products of combustion and the like which move into close proximity to the surface.

Although a sensitive probe is created, the magnitude of the charge is generally such that a high input impedance device which also has good electrometer characteristics is necessary to detect the signal. Generally, a FET (field effect transistor) detecting and amplifying unit provides a highly satisfactory system as shown in other prior art such as U.S. Pat. Nos. 3,754,219 and 3,989,463.

An electret is therefore defined herein as any dielectric or insulating material having a bulk resistivity of at least $1 \times 10^{12}$ ohm cm and a surface resistivity of $1 \times 10^{10}$ ohms/square, and which produces a permanent high intensity electric field as a result of an electric charge essentially permanently affixed to the electret, and which charge may be on or in the dielectric material. Thus, the electric field may result either from the appropriate alignment of the internal dipoles in the dielectric material or as the result of an electric charge deposited within or on the surface of the electret. Generally an electret material may be considered the electrostatic analogy of a permanent magnet, with the exception that the electret material may contain both electric dipoles and electric monopoles. This fundamental difference provides the basis for polarization of dielectric material to form an electret in various different methods and generally a greater number than that permitted in the polarization of a magnetic material. Thus, in the case of a dielectric material, the necessary charge and polarization may be created either by an applied electric field, by either electronic, ionic, or orientational polarization, or charge implanting. An electric field applied to the dielectric may generate relative displacement of positive and negative charges within an atom of the dielectric material, resulting in the induction of a dipole moment within the atom which originally had no charge or dipole moment. In addition, positively or negatively charged ions may be displaced relative to each other by the action of a field, thereby generating ionic polarization within the material. Such polarization however, is lost upon removal of the electric field. Various dielectric materials include molecules which have a permanent dipole moment and when an external electric field is applied to such material, the elementary molecules or portions of them tend to align with the dipoles in the direction of the field. When the field is removed, the molecules may remain in the aligned position within the dielectric material. Such dielectric materials having an internal field as a result of such dipole orientation are defined as including a heterocharge because the polarity of the surface charge is opposite that of the polarizing electrode. In addition to dipole moment alignment, charged particles or electrons can be introduced into the dielectric material or on the surface from an external source. Such internally generated charges have been deposited using a corona discharge or an electron beam. Such an externally charged electret, is defined as having a homocharge because the charges are implanted, have the same polarity as the polarizing electrode, and are all of the same charge.

The fabrication of the sensor element requires the intimate attachment of the electret to the compensating electrode as well as charging of the dielectric body to create the electret with the necessary field intensity over a substantial period of time.

SUMMARY OF THE PRESENT INVENTION

The present invention is particularly directed to the fabrication of electret sensing elements which include a compensating electrode member and a charged dielectric or electret body firmly affixed to the electrode member, which provides the basis for interconnecting of the sensor or sensing element in a sensing apparatus.

A dielectric body generally to be subsequently charged is affixed to the compensating electrode member by various methods such as vapor deposition of the electrode material, by lamination, adhesive bonding or baking a preformed compensating electrode member to a preformed dielectric body. In a particularly practical step, dielectric particles are applied to a compensating electrode member and subsequently heated to fuse the particles into a pore-free body and to intimately affix the body to such member. In all methods, a clean dielectric material and/or electrode material is required to create a firm connecting interface bond between the dielectric body and the compensating electrode member, and a primer coating may be applied to enhance the bond of the dielectric to the electrode. A next significant step is a careful thermal destressing of the dielectric material or body prior to the charging thereof, in order to eliminate any stress or strain deformation which may have occurred during the handling, manufacturing, and packaging of the dielectric material or its affixation to the compensating electrode. Further, after affixing of the compensating electrode member, the dielectric material is preferably tested to insure that no low resistance path exists and that the desired high bulk resistivity as well as the necessary surface resistivity are maintained. It is important that the dielectric body be free of low resistance paths.

The method of charging the dielectric body is not critical. An electron beam source provides one satisfactory means of the charging to form an electret. The depth of the charge penetration can be readily controlled by the electron beam voltage and uniform dispersion of the injected charge established by proper focusing of the electron beam. Electron beam equipment is relatively sophisticated and the charging system is therefore relatively expensive. The inventors have discovered that the simplest and most effective process for practical implementation with a high degree of reproducibility is a liquid charging process wherein liquid contact is made to the dielectric material and a high intensity field is created through the liquid to deposit a charge on or in the sensing surface of the dielectric body. The liquid should have a good wetting characteristic as well as a high rate of evaporation in order to create an electret with a uniform and high charge. The liquid contact may for example, be made using an applicator or by placing the dielectric surface within a charged liquid bath. It has been found that the charging cycle or procedure is further affected by the particular final step of creating the charge. The inventors have found for example, that a charged applicator moved relative to the dielectric surface and with a liquid bridging contact therebetween effectively charges the dielectric body. In such a process, a single wiping cycle and one continuous charging motion is more effective and contributes to formation of a stable electret. If the dielectric surface to be charged is placed into a charged liquid bath, the potential of the dielectric body is preferably made positive relative to the bath.

The present invention produces a reliable and practical method of fabricating a charged electret sensing probe unit which has a long, stable life and which may be processed and handled in the practical environments where combustion or pollutant detection are required.

DESCRIPTION OF THE ILLUSTRATED DRAWINGS

The drawings furnished herewith illustrate a preferred construction of the present invention in which the above advantages and features are clearly disclosed as well as others which will be clear from the following description of such embodiments.

In the drawings.

DESCRIPTION OF THE ILLUSTRATED EMBODIMENT

Figures 1, 2A, 3:
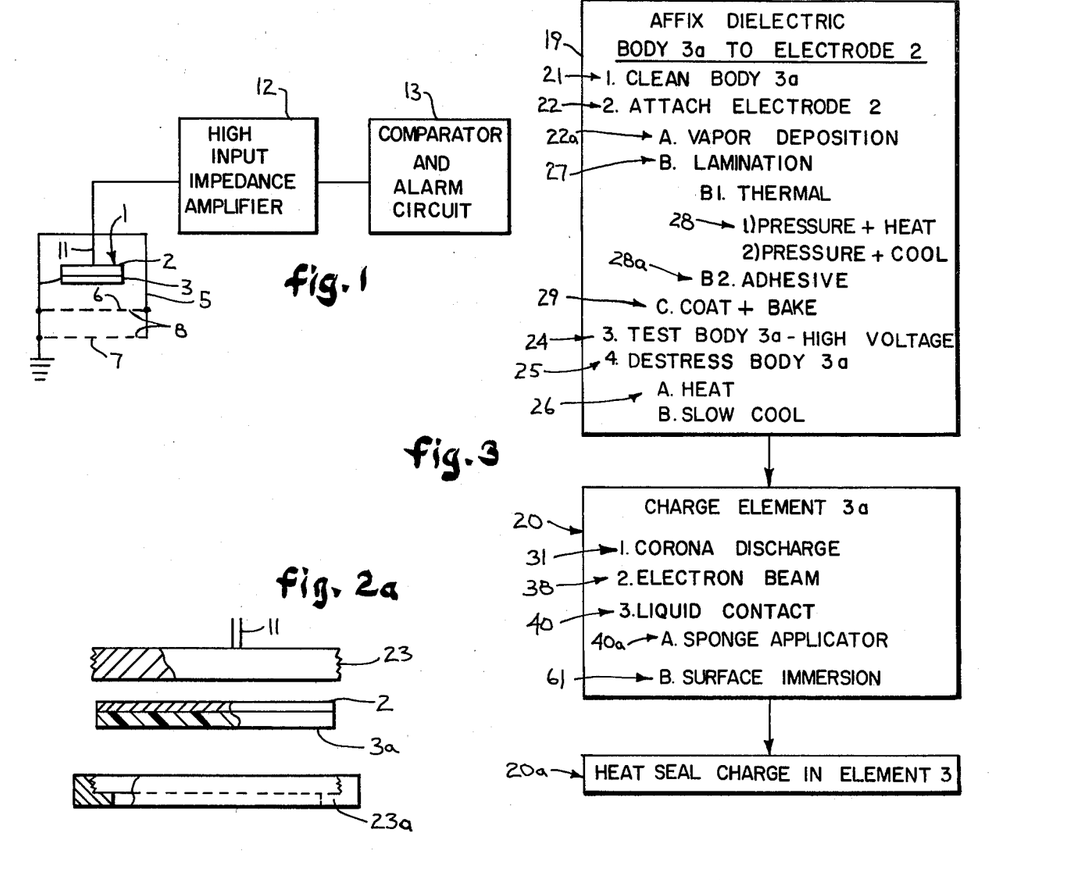
FIG. 1 is a diagrammatic illustration of a fire detection apparatus incorporating a sensing probe unit constructed as one embodiment of the present invention.
FIGS. 2 and 2a are enlarged views illustrating the sensing electrode or probe unit as shown in FIG. 1 and includes a special dielectric sensing surface.
FIG. 3 is a graphical illustration showing the steps in fabricating the dielectric sensing unit.
Figure 2:
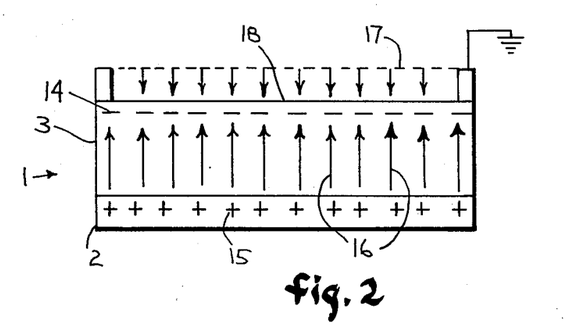

Referring to the drawings and, in particular to FIGS. 1-2, a sensing probe unit 1 which is fabricated in accordance with the teaching of the present invention, is shown including a metal compensating electrode plate 2 and an outer electret member 3 secured thereto. The probe unit 1 is shown as the sensor element of a fire detection unit in which the unit 1 is preferably mounted within an outer supporting housing or case 5 having a pair of cupshaped perforated plates or electrodes 6 and 7. Perforations 8 in both of the shielding electrodes 6 and 7 permit essentially free access of the surrounding environment into the interior of the housing and into contact with the special probe unit 1. In the illustrated embodiment of FIG. 1, the probe is a disc-like element including the metal plate 2 with a nonconductive and reactive material forming the electret member 3 secured to the exposed outer face thereof. A supporting post and terminal 11 is secured to the plate 2 and suitably supports the probe 1 properly located in close spaced relation to the shielding electrodes 6 and 7. The terminal 11 of probe unit 1 is connected as the input of a high impedance detection and processing circuit 12 as shown in FIG. 1, and operates a suitable alarm circuit 13 of any suitable construction.

Generally, the illustrated detection unit corresponds to that disclosed in the previously identified copending application and the novel probe unit 1 functions either as an electrostatic probe or as one plate of a capacitor sensor, to generate a small detectable electrical signal in the presence of gaseous products such as encountered in the incipient and following stages of combustion. The electronic processing circuit 12 may be of any suitable construction adapted to provide a high impedance input connection to the probe 1 such as generally disclosed in the above application, and no further illustration or description is given thereof.

The present invention is particularly directed to the fabrication of the probe unit 1 to create the required bonding of the metal compensating electrode 2 and the dielectric detection or electret member 3 which is formed to produce the special and unique response to the products of combustion including those created during the incipient and initial stages of combustion.

Referring particularly to FIG. 2, an enlarged diagrammatic illustration of the sensing electrode or probe unit 1 is shown. The probe unit 1 of this invention in one embodiment includes the initmate attachment of a preformed dielectric member or body 3, which is subsequently processed to form the electret body 3, to the compensating electrode 2 to form a probe subassembly, followed by charging of the dielectric body 3 to create an internal charge and/or a surface charge 14 and a compensating charge 15 of opposite polarity in the compensating electrode 2. The dielectric body, as subsequently discussed, may be preformed to the same shape and size as the electret 3, and is referenced herein by the number 3a to distinguish the bodies between the non-charged and charged state. The result of the charged dielectric or electret 3 of the probe unit 1 is the creation of the high intensity internal electric field 16 which functions in the sensor to significantly increase its response. The high intensity field 16 created by the charge carried by the dielectric body creates an induced field with an induced negative charge 17 on the gaseous products at the probe surface 18. The formation and attachment of the electret material is significant to prevent neutralization and loss of charge carried by a probe unit. The inventors have found careful fabrication and processing necessary to thereby create a probe having proper response and a significant operating life.

In one method, the fabrication procedure, as shown in FIG. 3, includes two basic sequences, the first of which is affixing the electrode 2 and a non-charged dielectric member or body 3a and the second of which is the charging of the dielectric body 3a to form electret 3, as shown at 19 and 20. A third basic step, which is preferably included to obtain optimum results, includes a final heating sealing step as shown at 20a.

The first sequence 19 in the fabrication of the electret and sensor probe unit 1 is a multiple step process for attaching the compensating electrode and dielectric body. The necessary attachment may, for example, be provided by vapor deposition of a compensation electrode, by a suitable adhesive or thermal bonding of a dielectric to an electrode element to establish the necessary intimate adhesion between the probe elements. In any and all of the affixing procedures, a conventional clean room processing is generally necessary for creation of an optimum final sensor element.

The surface of the preformed dielectric body or element is thus first thoroughly cleaned by any suitable process such as scrubbing or the like, as noted at 21 to remove surface deposits.

The dielectric material is preferably a polymeric material, and particularly anyone of those sold under the Du Pont trademarks, Teflon, including the TFE, FEP, and PFA types. Other materials and even mixtures of materials which have the appropriate characteristics may of course be used. Conventional cleaning of the "Teflon" body is satisfactory, such as by the use of a laboratory grade detergent-water mixture and a rinse with deionized water followed by a solvent rinse such as alcohol. The surface can be readily and thoroughly dried after cleaning through solvent evaporation.

The compensating electrode 2 may then be formed and attached in various methods, as noted at 22 in FIG. 3. In a first method, electrode 2 is formed by vapor deposition identified at 22a in FIG. 3, onto a polymeric film body 3a which may be a preformed thin, disc-like element and which may be mounted as shown in FIG. 2a. A contact plate 23 is adapted to abut the electrode 2. The edge of plate 23 is threaded to receive a clamp ring 23a having an outer clamp flange which abuts the edge of the element to clamp the disc-like element to plate 23. The supporting terminal plate 23 is secured to the deposited electrode plate 2 to permit connection to the detection output means as shown in FIG. 1 after the complete charging and processing of the subassembly.

In such a process, the cleaned and dried polymeric film 3a is placed in a suitable vacuum evaporator, not shown, under a vacuum on the order of $1 \times 10^{-6}$ torr. Such devices are well known and readily available and have not therefore been illustrated. A thin metal film is deposited by a conventional vapor depositing procedure. A preferred compensating electrode material would be essentially pure aluminum, which has a work function creating a minimum charge recombination in a charged electret as hereinafter discussed. Such a metal layer firmly and intimately adheres to a clean polymeric surface as a result of weak Van der Waal forces. The compensating electrode layer can be minute, generally on the order of 50 to 1,000 angstroms (A) thick. Although the thickness of the compensating electrode is not critical, a minimum acceptable thickness is that which establishes and maintains complete operative continuity over the surface of the sensing polymeric element.

The next step in the affixation process 19 preferably includes a high voltage breakdown test, as noted at 24 in FIG. 3.

The dielectric-electrode subassembly is subjected to a high voltage applied across the compensating electrode and sensing surface 18 to check for any low resistance path. Thus, it is essential for optimum manufacturing and functioning that there be no low resistance path between the sensing surface and the compensating substrate.

The next significant step in the fabrication process includes thermal destressing of the dielectric subassembly, as shown at 25. Packaging and handling of the dielectric body will normally result in certain stress and strain deformation of the dielectric material. The inventors have discovered that such deformation interferes with the ability of the dielectric to not only trap a charge but to hold a charge which has been created in the material. Thermal destressing may be readily provided by heating of the compensating electrode-dielectric subassembly and, thereafter slowly cooling of the subassembly to essentially avoid all thermal shock and thermal stress development as indicated at 26 in FIG. 3. For example, a vapor metallized polymeric subassembly may be heated in a suitable oven or the like, not shown, at 150° C. (approximately 300° F.) for a period of four hours. Thereafter the subassembly is slowly brought to room temperature (a temperature range of 60° to 100° F.) over a period of 1 to 24 hours, thereby avoiding thermal shock and thermal stress development.

The dielectric body 3a is now in condition for charging to convert the dielectric body into the necessary long life electret 3.

Before proceeding with the description thereof, laminating and baking processes to form the probe subassembly are briefly described.

In the lamination embodiment referenced at 27 in FIG. 3, the polymeric body or film 3a is bonded directly to a conductive metal substrate or plate 2, which may be of sufficient thickness to function as the compensating electrode and as the terminal means. The metal plate 2 therefore may be a film-like element or have a substantial thickness to which the connecting stud 11 is suitably connected. In this instance, the aluminum substrate or other metal plate is sand blasted or otherwise suitably processed to increase the adhesion characteristic. The cleaned and non-charged polymeric element 3a and the treated compensating metal plate are then mounted in a suitable laminating press which is capable of establishing a uniform pressure over the interface. Further, a heating unit is applied to the subassembly which is capable of creating uniform temperature distribution over the interface. A conventional laminating press capable of establishing pressure on the order of 100 pounds per square inch (PSI) and a temperature equal to the flow point of the polymeric material has been employed. Thus, with a FEP "Teflon" dielectric, the heating unit must create a temperature at least equal to 585° F. PFA "Teflon" requires a bonding temperature of 595° F. Further, a bonding agent may also be used. For example, for a TFE "Teflon" dielectric, a layer of FEP "Teflon" may advantageously be interposed at the interface to serve as a separate adhesive material. The temperature and pressure when brought up to the required minimums need only be held for a momentary period, on the order of 30 seconds to 30 minutes. Thereafter, the pressure is maintained while the temperature is slowly reduced to ambient or room temperature, as noted at 28 in FIG. 3. The reduction in temperature is carried out under a controlled sequence to minimize thermal shock or stressing. Thus, the temperature may be reduced from the order of 600° F. noted above to ambient room temperature of approximately 72° F. in 1 to 24 hours. Even then, the special thermal destressing sequence, as shown at 25 in FIG. 3, prior to charging is a desirable additional step which contributes to long life and stability. The laminated subassembly is now in condition for charging.

In the sensor fabrication, the polymeric material may be secured to a compensating electrode using a modified laminating process. In this instance an aluminum or stainless steel substrate which functions as the compensating electrode assembly and the connecting terminal, is also sand blasted or otherwise treated to enhance bonding. In addition, a primer is preferably applied to the metal substrate, to further enhance the adhesion with the polymeric layer or element during the laminating process. For example, with a TFE "Teflon" dielectric element a fluorocarbon primer has been used satisfactorily. After the application of the fluorocarbon primer, a disc-like film of TFE "Teflon" is bonded to the metal substrate with the application of heat and pressure as described above.

A preformed, thermally destressed, disc-like Teflon member may also be applied to the metal substrate with the use of an auxiliary adhesive, as noted at 28a in FIG. 3. For example, a thermally destressed TFE "Teflon" disc may be applied to the metal substrate with an adhesive, such as General Electric's Silgrip SR573 silicon adhesive. In this case a thin layer of Silgrip SR573 is applied to one surface of the metal substrate and one surface of the destressed Teflon disc, the solvent is allowed to evaporate from the adhesive by allowing the parts to stand undisturbed for at least 30 minutes, and then affix the silicone adhesive layers on each part together. This process does not lend itself to thermal destressing after bonding of the polymeric film and the metal substrate. Therefore, it is necessary to thermal destress the polymer disc-like member prior to adhesvie bonding it to the metal substrate. The thermal destressing may occur either before or after attachment of a dielectric body and as defined in the claims, cover either sequence unless specifically defined in a given sequence. Where appropriate, the destressing is done after attachment to minimize possible stressing during the handling and attachment process.

A further method or fabrication attachment step referenced at 29 in FIG. 3, may be used wherein the dielectric body or polymer layer 3a is attached by a coating and baking process. In this method, polymer particles, which may be in an aqueous or organic liquid carrier dispersion, are applied by any one of a number of means to a metal substrate member 2, the carrier liquid allowed to evaporate if present, and the deposited particles (powder layer) free of the carrier fluid baked onto the metal substrate member. Typical polymers in particle form include the Teflon materials such as TFE, FEP, and PFA. They may for example, be applied as dry powders by electrostatic spraying methods or by fluidized bed methods, or they may be applied as liquid dispersions by spraying or brushing techniques. When the particles are deposited on the metal substrate, the carrier liquid, if present, is allowed to evaporate, and the polymer particles are fused together and to the metal substrate by a baking operation at an elevated temperature for the particular particle material.

After affixation of the compensating electrode 2 to the dielectric body or element 3a, the subassembly is subjected to the voltage breakdown test and thermal destressing prior to charging of the dielectric element to establish long term stability.

After the subassembly is formed and thermally destressed, the subassembly is charged employing a suitable process for creation of an internal charge and/or an external surface charge capable of creating an external field with a typical intensity of $10.7 \times 10^3$ volts/cm for a distance of 0.32 cm. Although any detectable charge should enhance the sensitivity of a dielectric sensing member, $1 \times 10^2$ volts/cm at 0.32 cm is generally considered to be a lower limit for appreciable and practical effects. Of course, the upper limit is dictated by the dielectric material break down voltage level. The higher level of field intensity is desired to provide higher output response levels which permit more accurate detection and particularly with simpler electronic detection circuitry. Various charging processes such as triboelectric charging, corona discharge charging, electron bombardment charging and liquid contact charging are generally known charging methods.

Figure 4:
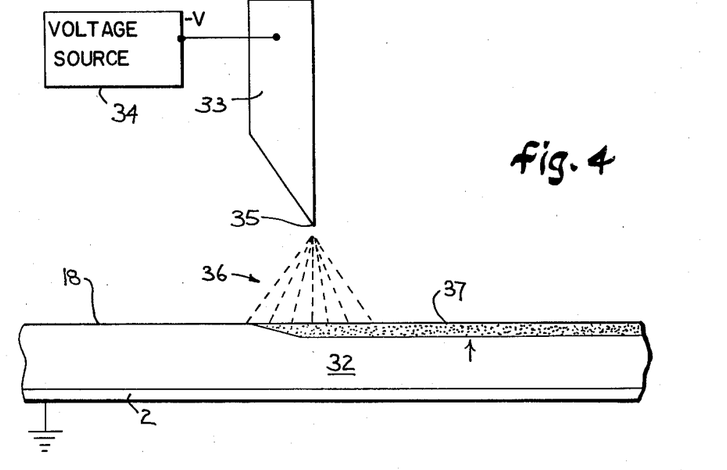
FIG. 4 is a diagrammatic illustration of a charging apparatus using corona discharge for charging.

Triboelectric charging is basically a contact charging method relying on the friction between the dielectric surface and a conductor. The process is not readily understood and the only significant advantage is simplicity. Corona charging provides a somewhat more practical method, referenced at 31 in FIG. 3 and diagrammatically illustrated in FIG. 4. The dielectric subassembly 32 is accurately positioned in a close spaced relation to a conductive knife edge electrode 33. A suitable high voltage power source 34 is connected between the knife edge electrode 33 and the subassembly, and the knife edge 35 is held at a very high negative potential, generally on the order of multiple kilovolts. In a practical application, the subassembly may have a thickness on the order of 0.010 inch. The knife edge electrode 33 is located with its lower effective sharp edge 35 spaced from the sensing surface 18 of the dielectric by a distance of 0.050 inch, defining the corona discharge region 36 therebetween. The output of the potential source is set such that the knife edge is held at a voltage of −4 to −6 kilovolts (KV) and the dielectric moved past the high voltage knife edge 35. The corona discharge from the knife edge 35 ionizes the air molecules and generates free electrons in the intense electric field created between the knife edge and the dielectic unit. As the dielectric element moves beneath the knife edge 35, the surface is bombarded with ions as well as free electrons. The result is a surface charged layer or portion 37 which extends into the dielectric body or element. Although this provides a relatively simple charging apparatus, the corona discharge is significantly dependent on atmospheric parameters such as water vapor and the like which might be present. Therefore, the process does not provide a high degree of reproducibility in successively formed and mass produced units.

An electron beam process, referenced at 38 in FIG. 3, produces a similar charge. For example, an electron beam may be formed using a conventional heated filament in a vacuum of $1 \times 10^{-5}$ torr. The electron beam is aligned with the dielectric assembly which is connected to a positive voltage supply and functions as an anode. Electron beam systems are well known and available and permit rather closely controlled charging of the polymeric materials. The depth of the charge for example, can be accurately controlled based on the choice of the electron beam voltage and the formation of an injected charge can be rather carefully controlled by appropriate focusing of the electron beam. The intensity of the injected charge can be controlled by the combination of the magnitude of the electron beam current and the exposure time.

In this method, substantially all of the electrons generated do engage and strike the dielectric surface of the subassembly and are therefore incorporated into the dielectric body.

In a practical implementation, a dielectric-electrode subassembly is inserted into a transmission electron microscope, with the subassembly replacing the microscopes conventional film plate.

Although the various parameters can be carefully controlled, fairly sophisticated equipment must be used to provide the desired control. One significant disadvantage therefore of the electron beam charging system is the rather costly and complicated vacuum charging apparatus and related controls which must be employed.

The inventors have found that a particularly satisfactory and practical charging implementation for an electret sensor uses a liquid contact charging method, as referenced at 40 in FIG. 3, in which the dielectric surface 18 is provided with a liquid cover and charging is created by applying a high voltage across the liquid and the dielectric body. The liquid creates intimate contact to the dielectric sensing surface 18 while the metal compensating electrode 2 completes the circuit. This has been found to be the simplest method while maintaining effective charging of the dielectric and with a high degree of reproducibility.

Figures 5, 6:
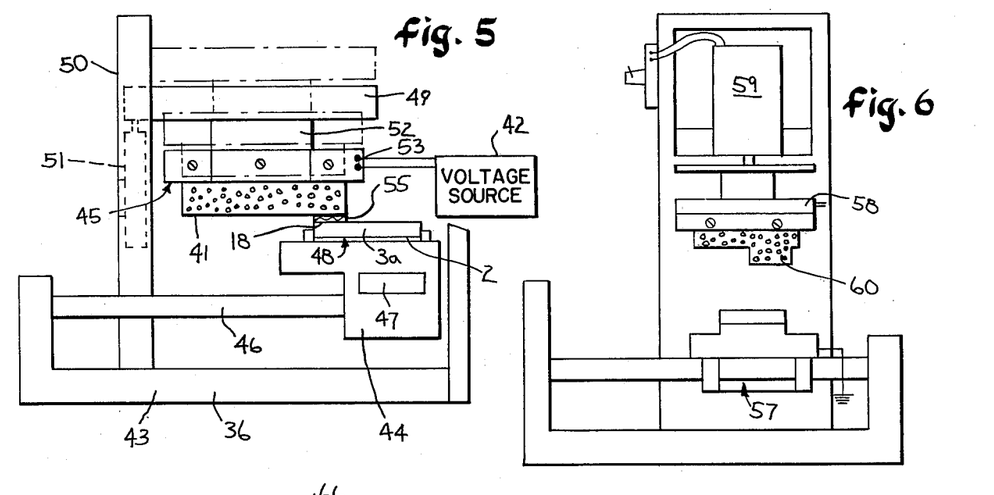
FIG. 5 is a diagrammatic illustration of a charging apparatus using a sponge applicator for liquid contact charging.
FIG. 6 is a view similar to FIG. 5 of an alternate sponge applicator apparatus.

A satisfactory method, referenced at 40a in FIG. 3 and diagrammatically illustrated in FIG. 5, uses a high voltage sponge element 41, with relative movement across the dielectric sensing surface 18. The sponge member 41 is shown selected with a width equal to the width of the dielectric area of surface 18 to be charged. A high voltage supply 42 is of course connected across the sponge and the dielectric body during the movement. In the illustrated embodiment, the charging apparatus includes a supporting base structure 43 with a table 44 slideably mounted beneath a sponge holder 45. The table 44 is shown mounted on a suitable linear sliding shaft or journal 46 and coupled to a suitable piston actuator or motor means 47 for linear movement beneath the sponge holder.

The table 44 includes a releasable support means for the dielectric subassembly 48. The table and particularly the support portion for the dielectric subassembly is connected to power supply ground, to correspondingly connect the compensating electrode 2 to ground. The sponge applicator or member 41 is secured within the holder 45, which is movable vertically for location in intimate coupling to the surface of the dielectric member 31. The illustrated sponge holder 45 is mounted in a vertically moving support arm 49 which is carried by a vertical post member 50. A vertically oriented piston-operator 51 is connected to position arm 49 and thereby sponge 41. A high voltage insulating block 52 is interposed between the support arm 49 and the holder 45. The high voltage source terminal 53 is attached directly to the holder 45. The high voltage holder 45 with the terminal 53 is thus electrically isolated from the support arm 49.

Thus, dielectric-electrode subassembly 48 is mounted on the table 44 with surface 18 in spaced parallel and opposed relation to sponge 41.

The sponge 41 is saturated with a suitable charging liquid and moved downwardly into close spaced relation to the dielectric subassembly and establishes a bridging liquid contact 55 shown between the dielectric surface 18 and the sponge 41. Thus, the sponge 41 is located during the charging cycle sufficiently close to the surface to avoid actual physical contact, as shown enlarged in FIG. 5, but still sufficiently close to establish a liquid contact pressure and charge transfer fluid interface. Although the liquid contact pressure is not critical, it does affect the wetting characteristics as well as the evaporation rate of the liquid and must be considered, as presently discussed.

The holder 45 is energized and charging table motor 47 is operated to move the subassembly beneath the energized sponge 41. The high voltage across the liquid 55 results in a charge transfer into the dielectric.

The sponge may be selected of any suitable material but is preferably non-conductive and non-reactive with the charging liquid. For example, a highly satisfactory material is a TFE Teflon fiber belt material which is sold under the trademark Armalon by Du Pont Company. Such material has been found to be very stable and non reactive with a preferred charging liquid, TMC Freon, as well as other volatile fluids.

Thus, the charging liquid 55 may be any suitable liquid which has an appropriate high resistivity, wetting characteristic and rate of evaporation. The effective charge transfer results from good liquid contact. Further, if the liquid has a high rate of evaporation, there will be a very rapid removal of the liquid from the dielectric surface after separation from the sponge. A rapid evaporation rate also minimizes droplet formation on the dielectric surface.

After voltage removal, the dielectric surface areas which were not liquid contacted or on which liquid droplets form, may not be fully charged. Consequently, the surface will not present a uniform charge field and the output or response of the sensor may not indicate the gaseous pollutant or combustion products to the desired degree of accuracy. The rapid removal of the liquid is also important to retention of maximum charge separation which is promoted by removing of the liquid while the polarizing voltage is present. The rapid and even evaporation of the liquid as the sponge moves from a surface area tends to create such a state.

Various liquids were evaluated including water, ethyl alcohol and various types of liquid fluorinated hydrocarbons, particularly those which are sold under the trademark Freon. Of the several liquids used, Freon produced the best results; apparently because of its excellent wetting characteristic and its very rapid rate of evaporation as well as the necessary order of high electrical resistivity. The following Freon liquids were used as charging liquids and are listed in the order of the highest evaporation rates:

| Fluid | Boiling Point | % additive to Freon TF |
| --- | --- | --- |
| TMC (AZ) | 36.2° C. | 50% Methylene Chloride |
| TMS (AZ) | 39.7° C. | 6% Methanol, Stabilized |
| TA (AZ) | 43.6° C. | 11% Acetone |
| TE (AZ) | 44.6° C. | 4% Ethanol |
| TE-35 * | 48.3° C. | 35% Ethanol |

(AZ) = Azeotrope with Freon TF
* = Blend with Freon TF; non-azeotropic

TMC Freon appeared to produce a superior product. TMC Freon contains 50% methylene chloride and 50% Freon TF, and is an azeotrope liquid. TMC Freon has a relatively low boiling temperature of 36.2° C. resulting in rapid evaporation of the liquid without a change in its composition.

In operation, the table is located to one side of the sponge holder and the sponge. The dielectric subassembly is mounted on the charging table with the compensating electrode 2 in intimate contact with the support and thus to ground. The power is supplied to the sponge holder, and thereby to the liquid in the sponge. The holder is moved down to locate the sponge just above the top plane of the top surface of the dielectric member 31 and the table is then moved beneath the sponge at an appropriate rate such as 0.5 feet per minute to insure the appropriate charge transfer and charge migration which occurs through the liquid and into the dielectric material.

Although not critical, the inventors have discovered that multiple cycles appear to adversely effect the final charge state of the dielectric body. Generally, a single cycle with a single directional movement produced the optimum charge in the dielectric body. Apparently repeated charging of the same area creates unstable secondary electrons on the surface or within the dielectric. Such electrons in turn decrease the stability of the final electret.

The best relative speed of the charging sponge across the dielectric surface will vary with the saturation of the sponge and the evaporation rate of the charging liquid. If insufficient liquid is present, an ineffective or low charge transfer is created. On the other hand, excessive quantities of liquid may result in a liquid droplet formation on the surface, with a resulting loss of charge and particularly a non-uniform charge and a resulting non-uniform sensor response.

A circular charging motion can also be used. A suitable apparatus is shown in FIG. 6 in which a fixed table 57 is located in spaced relation to a rotating sponge holder 58. In this embodiment, the sponge holder is coupled to a reversible rotating drive motor 59. A sponge 60 is of a length substantially equal to the radius of the dielectric area to be charged. The sponge 60 is moved into close liquid coupling to the properly located dielectric subassembly and the motor 59 energized to provide the desired directional rotation of the sponge. As in the linear charging method, the rotary method preferably includes a single charging cycle, with a single 360° rotation of the sponge over the dielectric unit.

Figure 7:
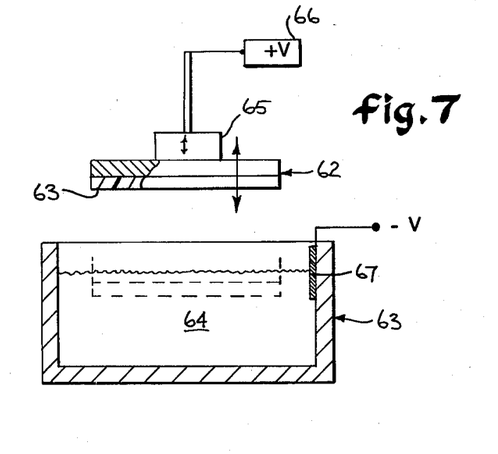
FIG. 7 is a diagrammatic view of liquid bath charging apparatus.

Although the wiping method has been satisfactorily used, an immersion charging apparatus and method, as referenced at 61 in FIG. 3, should provide an improved mass production technique. For example, as diagrammatically shown in FIG. 7, an uncharged dielectric subassembly 62 may be mounted in overlying relationship to a confined bath 63 of a charging liquid 64. The subassembly 62 is carried by a vertically movable support 65 which is coupled to the high voltage source 66, with the opposite side thereof connected through a suitable electrode 67 to the immersion bath. Although either high voltage polarity can be employed, the surface immersion bath 63 is preferably held at a negative potential with respect to the dielectric body or subassembly 3a. This has been found to enhance the stability of the electret produced. In operation, the dielectric subassembly is moved downwardly into engagement with the charging liquid 64, as shown in phantom, and the high voltage is then applied across the interface for a desired period. With the high voltage applied, the dielectric subassembly is moved upwardly from the charging liquid 64 to expose the surface to the surrounding atmosphere.

The charging voltage is preferably as high as the material will withstand because the resulting electric field of an electret is generally proportional thereto.

The maximum charging voltage which will be applied is of course less than the breakdown voltage of the dielectric material. Generally, the charging voltage is also affected by the thickness of the dielectric material. Variations of thickness and voltages were studied for electric field intensities in the range of 50 to 500 volts per mil of thickness range. Generally it was found that the use of 340 volts per mil provided satisfactory results. Typical sensor subassemblies which were made include a 0.010 inch thick dielectric sensor unit charged at 1.7 kilovolts.

In general, the effectiveness of the charging step is determined from the following functional characteristics of the charged subassembly:

1. The uniformity of the injected charge in and/or on the dielectric element;

2. The resulting injected charge voltage of the dielectric in comparison to the applied charging voltage; and 3. The charge voltage decay of the charged dielectric unit with respect to time.

Thus, the three most significant factors are the charge uniformity, the charging efficiency of the fabrication charging method, and finally the stability of the charged dielectric element. Generally, the final charge of the electret should be within a few percentage points of the original charging voltage. An actual analysis has found that typical values for charging efficiencies using the liquid charging method were in excess of 92%.

In the fabrication of the electret sensor unit, heat sealing of the charged electret improves the life. In this step, the charged electret unit is mounted in a suitable oven and held at temperatures from 50° to 100° C. (centigrade) for a time period ranging from several minutes to more than four hours. The final step is diagrammatically illustrated in FIG. 8 in which the charged dielectric unit 62 is mounted within an oven unit 68 having a suitable electric heating element 69 or the like. The inventors discovered that moderate heating which is defined as a temperature range of 120° to 225° F., tended to stabilize the electret sensor. In such final processing and heating, a protective ion shield 70 is mounted over and around the charged electret to eliminate the possible neutralization of the charge in and/or on the electret from ions generated by the oven heating elements.

Figure 8:
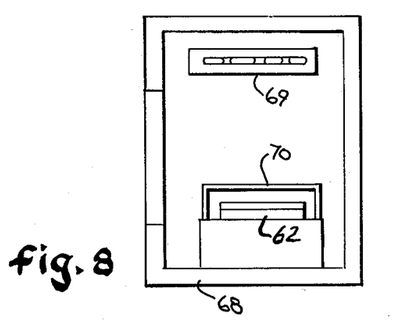
FIG. 8 is a diagrammatic view of a thermal destressing unit.

Subsequent to the above heat sealing step, the subassembly is preferably cooled at a relatively slow rate. Although the precise cooling rate is not critical, a rate in the range between 10° and 50° F. per hour are practical, useful and avoid detrimental changes in the final probe unit.

In the storage of a charged electret probe or sensor unit, care is desired to prevent the loss of the field within the electret, and in particular to maintain the compensating charge in the compensating electrode. Thus, outside influences can noticeably affect the electrostatic field and therefore its stability. Generally the decay of the electret with outside influences appears to be related to a loss of compensating charge. When compensating charge is lost, surface charge neutralization may occur. It is therefore necessary to provide proper storage as well as have configurations which will maintain termination of the induced charge lines of flux on the compensating electrode. Thus, the element is desirably stored in a suitable protective enclosure to prevent coupling or contact with the sensing surface by charge neutralizing elements.

The charged electret is preferably incorporated into an electric sensing assembly including an outer shielding assembly such as disclosed in applicant's previously identified copending application. Thus, a shield is located in close spaced relation to the electret probe and particularly the dielectric sensing surface. This enhances the sensitivity of the sensing assembly.

Various modes in carrying out the invention are contemplated as being within the scope of the following claims, particularly pointing out and distinctly claiming the subject matter which is regarded as the invention.

We claim:

1. The method of fabricating a non-conductive, gas sensing probe unit having an electrically non-conductive outer charged polymeric dielectric layer defining an exposed sensing surface and said charged dielectric layer having a permanent electric charge and being intimately bonded to a compensating conductive electrode, comprising at least the three separate steps of prefabricating a solid dielectric body having a bulk resistivity of at least $1 \times 10^{12}$ ohm cm at 50% RH and a surface resistivity of at least $1 \times 10^{10}$ ohms/square at 50% RH, thereafter thermal destressing of said prefabricated solid dielectric body, said thermal destressing including heating of said prefabricated solid dielectric body and then slowly cooling of said prefabricated solid dielectric body at a rate which avoids stress and strain deformation in the solid dielectric body to produce an essentially charge free dielectric body free of stress and strain, thereafter charging the destressed and charge free dielectric body subsequent to said destressing step to create a permanent electric charge in said body which creates a high intensity electric field at the exposed sensing surface, and including the step of bonding a compensating conductive electrode to the dielectric body without change in the permanent charge of said destressing dielectric body to form a dielectric-electrode electret subassembly.

2. The method of claim 1 including a final step of moderately heating the charged dielectric-electrode subassembly and slowly cooling the subassembly to stabilize charge within the charged dielectric body.

3. The method of claim 1 wherein said body is charged to a level sufficient to establish an electric field at the surface of the electret at least equal to $1 \times 10^2$ volts/cm at 0.32 cm.

4. The method of claim 1 including measuring the resistance of the dielectric material prior to charging to assure the absence of low resistance paths.

5. The method of claim 1 including the steps of physically cleaning said interface surfaces before affixing said compensating electrode to said dielectric body.

6. The method of claim 1 where said compensating electrode is formed by vapor depositing a highly conductive metal conductor upon a preformed dielectric body.

7. The method of claim 1 where said dielectric layer is formed by coating a preformed conductive electrode with dielectric particles to form said dielectric body and heating the composite structure to effect fusion of the particles to themselves to obtain an integral pore-free dielectric body and to effect bonding of the dielectric body to the conductive electrode.

8. The method of claim 1 wherein a primer material is applied to the conductive electrode, and said dielectric material is applied to the primer material.

9. In the method of claim 1 wherein said charging of said dielectric body includes the step of establishing a liquid film between a charging electrode means and said dielectric sensing surface, applying a high voltage source between said charging electrode means and said dielectric compensating subassembly across said liquid film, and separating the charged dielectric body from the liquid film.

10. In the method of claim 9 wherein said liquid is selected having good wetting properties, high evaporation rate, and high resistivity, and wherein the step of separating the body from said liquid includes rapid evaporation of the liquid from said sensing surface.

11. In the fabrication of a probe unit responsive to pollutants and to the products of combustion including those created during the incipient and initial stages of combustion, said probe unit including a base compensating metal electrode secured to an electret detection member having an exposed surface opposite the face secured to said metal electrode, comprising at least the three separate steps of fabricating an essentially non-charged dielectric solid body of a polymeric material to the configuration of the electret detection member, intimately affixing a metal electrode to the noncharged dielectric body to form a dielectric-electrode subassembly, thereafter thermal destressing the non-charged dielectric solid body by heating of said solid body and slowly cooling said heated solid body at a rate which avoids stress and strain deformation in said solid body to thereby create an essentially charge free dielectric body free of stress and strain, and applying a high intensity electron source to the sensing dielectric surface of the destressed and charge free dielectric body subsequent to said thermal destressing of said solid body and thereby creating a permanent electric charge carried by the solid body as a result of said high intensity electron source to form an electret and an electret-electrode subassembly.

12. In the method of claim 11 including the step of subjecting the non-charged subassembly to a high voltage breakdown test prior to destressing to detect any low resistance path between the sensing surface and the compensating electrode.

13. The method of claim 11 wherein said thermal destressing includes heating of the non-charged subassembly and slowly cooling of the subassembly to avoid essentially all thermal shock and thermal stress development.

14. The method of claim 11 wherein the thermal destressing includes heating the subassembly in an oven at substantially 300° F. for a period of substantially four hours, slowly cooling the subassembly to a temperature in the range of 60° to 100° F. over a period of at least one hour to thereby avoid any significant thermal shock and thermal stress development.

15. In the method of claim 11 or 13 including the step of subsequently heating the charged electret-electrode assembly to a moderate temperature, and thereafter slow cooling of the heated electret-electrode assembly.

16. The method of claim 11 including the step of scrubbing the electrode surface with a laboratory grade detergent-water mixture prior to attachment of the dielectric body to clean the surface.

17. The method of claim 11 wherein said dielectric body is formed of a polymeric material.

18. The method of claim 17 wherein said polymeric material is polytetrafluoroethylene.

19. The method of claim 11 wherein said compensating electrode is formed by vapor deposition of essentially pure aluminum on a polymeric body, said compensating electrode having a minimum thickness which establishes and maintains complete continuity over the surface of the sensing surface.

20. The method of claim 19 wherein the compensating electrode is deposited to a thickness in the range of 50 to 1,000 Angstroms.

21. The method of claim 11 wherein said dielectric body is formed by depositing dielectric particles on a compensating electrode, and heating said deposited particles and electrode to fuse the particles to a pore-free dielectric body and to fuse the dielectric body to the electrode.

22. The method of claim 21 including creating a dispersion of said particles in a fluid carrier and applying said dispersion onto said electrode, and removing the fluid carrier from the deposited particles.

23. The method of claim 21 including heating the charged subassembly to a moderate temperature and slowly cooling said subassembly to heat seal said charge.

24. In the method of claim 11 wherein the electrode is affixed by laminating a conductive substrate of sufficient thickness to function as the compensating electrode and as the terminal means to the dielectric body.

25. In the method of claim 24 wherein the electrode is a metal plate and including sand blasting the plate to increase the adhesion characteristic, placing the cleaned and non-charged dielectric body and the treated metal plate in abutting engagement, applying a uniform pressure over the interface, and heating the subassembly and creating a uniform temperature distribution over the interface equal to the flow point of the dielectric material.

26. In the method of claim 25 wherein the dielectric body is formed of a polytetrafluoroethylene dielectric, and including the step of interposing a bonding film at the interface to serve as a separate adhesive material.

27. The method of claim 26 wherein the adhesive material is actuated by heat.

28. The method of claim 26 wherein the adhesive material is actuated by solvent evaporation.

29. The method of claim 25 wherein said temperature and pressure are created for a period on the order of minutes, and maintaining said pressure while the temperature is slowly reduced.

30. The method of claim 11 wherein the conducting electrode is a substrate having a connecting terminal, and including the steps of blasting said substrate with particles to thoroughly clean the surface, applying a primer to the metal substrate to further enhance the adhesion with a dielectric body, applying the dielectric body in intimate contact with the substrate, and baking the subassembly to affix the compensating electrode to the dielectric body.

31. The method of claim 30 including applying the dielectric body as a layer of dielectric particles, said baking fusing said particles into a pore-free dielectric body.

32. The method of claim 30 including applying a breakdown voltage prior to charging of the dielectric body.

33. In the method of claim 11 wherein the subassembly is positioned in close spaced relation to a conductive knife edge electrode, and a high voltage means is connected between the knife edge electrode and the subassembly to create a corona discharge region therebetween, said corona discharge ionizing the air molecules and generating free electrons in an intense electric field, relatively moving the knife edge and dielectric body to bombard the sensing surface with ions and electrons to create a surface charge layer or portion which extends into the dielectric body.

34. The method of claim 11 wherein said charging step includes creating an electron beam focused on the sensing surface of the dielectric subassembly which is connected as an anode, whereby the electrons generated strike the dielectric surface of the dielectric body and enter and are incorporated into the dielectric body.

35. In the method of claim 11 wherein said charging step includes establishing a liquid covering the sensing surface of the dielectric body, applying a high intensity electric voltage across the liquid to develop a permanent electric charge carried by the dielectric body, removing the dielectric body from the liquid, said liquid having a high electrical resistivity and rapidly evaporating from the sensing surface in order to create an electret with an uniform charge and high charge level.

36. The method of claim 35 wherein said liquid surface is created between a liquid saturated applicator and the dielectric surface.

37. In the method of claim 36 wherein the applicator is smaller than the dielectric surface and relative motion is established to pass the applicator over the dielectric surface in a single pass.

38. In the method of claim 35 wherein the dielectric surface is placed into a charged liquid bath, and a potential source is connected to the bath and dielectric body.

39. In the method of claim 38 wherein the dielectric body is held at a positive potential relative to the bath.

40. The method of claim 35 in which said charging liquid is a fluorocarbon liquid.

41. The method of claim 35 in which said charging liquid is an azeotropic blend of two or more materials.

* * * * *